(12) United States Patent
Nagamizu et al.

(10) Patent No.: US 12,082,777 B2
(45) Date of Patent: Sep. 10, 2024

(54) ENDOSCOPE

(71) Applicant: OLYMPUS CORPORATION, Hachioji (JP)

(72) Inventors: Hiroyuki Nagamizu, Sagamihara (JP); Shun Ogi, Hachioji (JP)

(73) Assignee: OLYMPUS CORPORATION, Hachioji (JP)

( * ) Notice: Subject to any disclaimer, the term of this patent is extended or adjusted under 35 U.S.C. 154(b) by 537 days.

(21) Appl. No.: 17/402,805

(22) Filed: Aug. 16, 2021

(65) Prior Publication Data

US 2021/0369088 A1 Dec. 2, 2021

Related U.S. Application Data

(63) Continuation of application No. PCT/JP2019/005890, filed on Feb. 18, 2019.

(51) Int. Cl.
*A61B 1/00* (2006.01)
*A61B 1/04* (2006.01)
(Continued)

(52) U.S. Cl.
CPC ...... *A61B 1/00096* (2013.01); *A61B 1/00158* (2013.01); *A61B 1/00188* (2013.01); (Continued)

(58) Field of Classification Search
CPC ............ A61B 1/00091; A61B 1/00094; A61B 1/00096; A61B 1/00158; A61B 1/00188; (Continued)

(56) References Cited

U.S. PATENT DOCUMENTS

2008/0025159 A1\* 1/2008 Takayama .............. G02B 7/005
369/13.17
2008/0272869 A1\* 11/2008 Takayama .......... A61B 1/00188
335/219

(Continued)

FOREIGN PATENT DOCUMENTS

DE 102017107397 A1 10/2018
EP 2175458 B1 1/2013
(Continued)

OTHER PUBLICATIONS

International Search Report dated May 21, 2019, issued in counterpart application No. PCT/JP2019/005890 (2 pages).

*Primary Examiner* — Aaron B Fairchild
*Assistant Examiner* — Stephen Floyd London
(74) *Attorney, Agent, or Firm* — WHDA, LLP

(57) ABSTRACT

An endoscope includes a distal end portion in which an optical unit and a treatment instrument channel are held such that a photographing optical axis, a central axis of the distal end portion, and a central axis of the treatment instrument channel are linearly aligned When viewed from an end face of the distal end portion. The first magnet and the second magnet are arranged at non-rotationally-symmetric positions with respect to the photographing optical axis, and a region of the optical unit, which is on a side where a distance between the first magnet and the second magnet on an arc of a circle around the photographing optical axis is short, faces the treatment instrument channel.

8 Claims, 13 Drawing Sheets

(51) Int. Cl.
*G02B 23/24* (2006.01)
*G02B 23/26* (2006.01)

(52) U.S. Cl.
CPC .............. *A61B 1/04* (2013.01); *G02B 23/243* (2013.01); *G02B 23/26* (2013.01)

(58) Field of Classification Search
CPC   A61B 1/0019; A61B 1/0057; G02B 23/2438; G03B 2205/0046; G03B 2205/0069
See application file for complete search history.

(56) References Cited

U.S. PATENT DOCUMENTS

| | | | |
|---|---|---|---|
| 2009/0303619 A1* | 12/2009 | Iwasaki | G02B 23/243 |
| | | | 310/306 |
| 2011/0234781 A1* | 9/2011 | Hackel | A61B 1/042 |
| | | | 348/66 |
| 2013/0193778 A1* | 8/2013 | Wieters | A61B 1/00133 |
| | | | 310/12.04 |
| 2015/0287508 A1 | 10/2015 | Wieters et al. | |
| 2016/0018625 A1* | 1/2016 | Morishima | G02B 7/102 |
| | | | 359/824 |
| 2016/0041381 A1* | 2/2016 | Makiyama | G02B 23/2438 |
| | | | 359/824 |
| 2016/0213239 A1* | 7/2016 | Fujii | A61B 1/00163 |
| 2017/0065157 A1* | 3/2017 | Iwasaki | G03B 13/34 |
| 2017/0123181 A1* | 5/2017 | Fujisawa | G02B 23/2476 |
| 2018/0049621 A1 | 2/2018 | Iguchi et al. | |

FOREIGN PATENT DOCUMENTS

| | | |
|---|---|---|
| JP | 2000-037343 A | 2/2000 |
| JP | 2000-292712 A | 10/2000 |
| JP | 2002-189162 A | 7/2002 |
| JP | 2004-097292 A | 4/2004 |
| JP | 2016-509490 A | 3/2016 |
| WO | 2014/094970 A1 | 6/2014 |
| WO | 2014/203626 A1 | 12/2014 |
| WO | 2015/093398 A1 | 6/2015 |
| WO | 2016/166857 A1 | 10/2016 |
| WO | 2019/008769 A1 | 1/2019 |

* cited by examiner

ENDOSCOPE

CROSS-REFERENCE TO RELATED APPLICATION

This application is a continuation application of PCT/JP2019/005890 filed on Feb. 18, 2019, the entire contents of which are incorporated herein by this reference.

BACKGROUND OF THE INVENTION

1. Field of the Invention

The present invention relates to an endoscope including an optical unit configured to vary an optical focal position by causing a movable frame holding a movable lens to move forward and backward in an optical axis direction by a magnetic force.

2. Description of the Related Art

Conventionally, an endoscope including an optical unit has been well-known, in which the optical unit is capable of switching a focal position by causing a movable frame including inside thereof a movable lens to move forward and backward in an optical axis direction of an optical system. As a configuration of such an optical unit capable of switching a focal position, a configuration including an electromagnetic actuator is publicly known.

Japanese Patent Application Laid-Open Publication No. 2004-97292, for example, discloses, as a configuration for causing a lens barrel (movable frame) incorporated in an optical unit of an image pickup apparatus for endoscope to move forward and backward in an optical axis direction, a configuration in which a coil (electromagnetic coil) wound around a central axis of the movable frame and a pair of magnets arranged so as to he symmetric with respect to the central axis of the movable lens are arranged sequentially in a radially outward direction of the movable lens. The optical unit including the electromagnetic actuator as described above is applicable also to an image pickup unit disposed in a distal end portion of an insertion portion of an endoscope, for example.

SUMMARY OF THE INVENTION

An endoscope according to an aspect of the present invention is an endoscope including, in a distal end portion of an insertion portion, an optical unit and a channel. The optical unit includes: a Fixed lens barrel (fixed frame) made of a non-magnetic material; a Movable lens barrel (movable frame) made of a magnetic material and configured to hold one or more lenses that constitute a photographing lens, the movable frame being arranged movably in the fixed frame; and an actuator configured to drive the movable frame along an optical axis of the photographing lens. The actuator includes a coil wound around the fixed frame, and a first magnet and a second magnet that are arranged, in a protruded manner, on an outer circumference of the coil. The first magnet and the second magnet are arranged at non-rotationally-symmetric positions with respect to the optical axis, and a region on the outer circumference of the coil faces the channel, the region being on a side where a distance between the first magnet and the second magnet on the outer circumference of the coil is short by non-rotationally-symmetric arrangement of the first magnet and the second magnet.

DETAILED DESCRIPTION OF THE PREFERRED EMBODIMENT(S)

Figure 1:
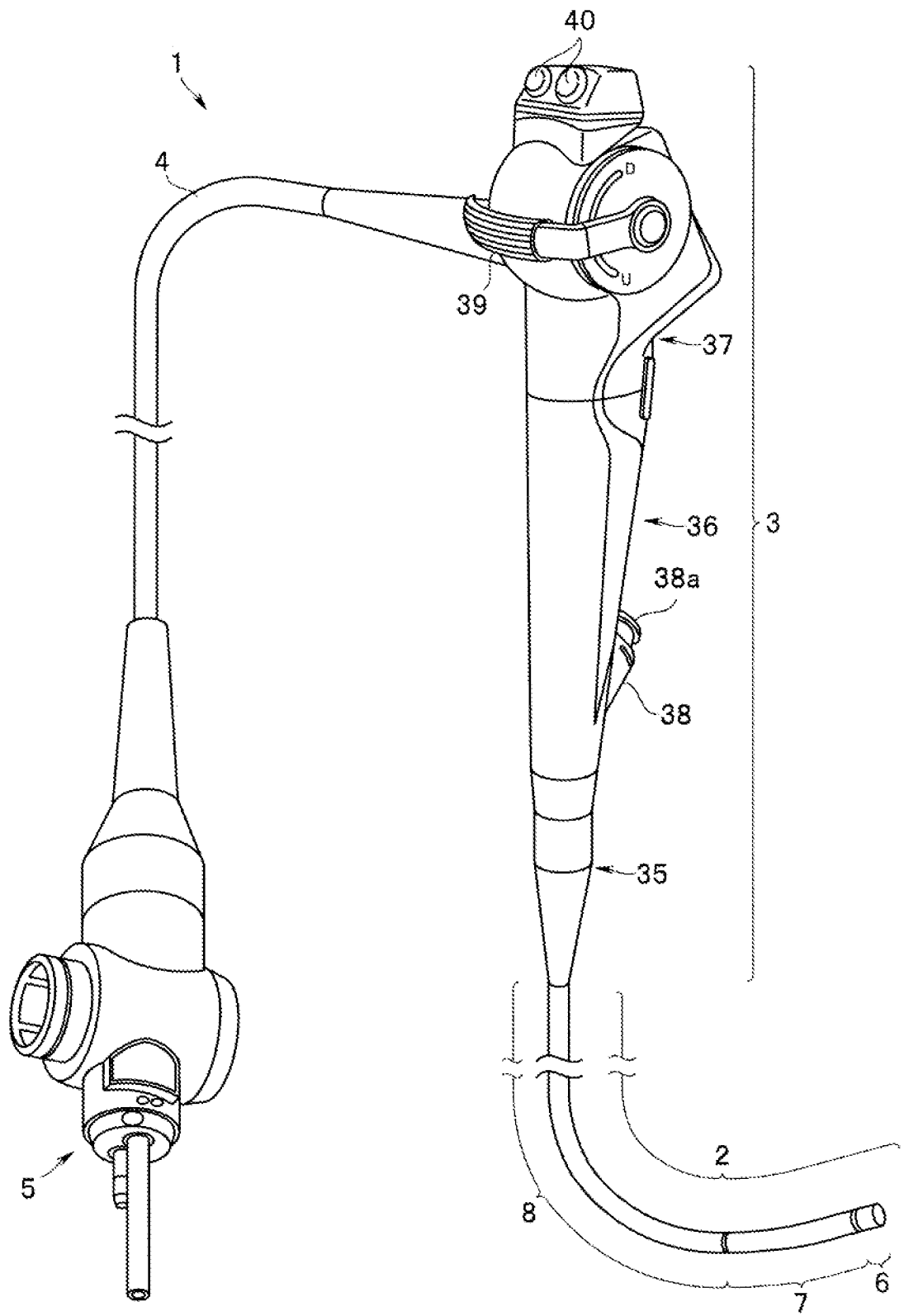
FIG. 1 is an appearance perspective view of an endoscope.

Hereinafter, an embodiment of the present invention will be described with reference to drawings. FIG. 1 is an appearance perspective view of an endoscope. The endoscope 1 illustrated in FIG. 1 is an endoscope for urinary organs such as a renal pelvis (pyeloureteroscope), for example.

The endoscope 1 includes an insertion portion 2 having an elongated (long) shape and configured to be inserted into a body cavity of a subject, an operation portion 3 provided at the proximal end of the insertion portion 2, and a universal cable 4 extended from the proximal end of the operation portion 3.

As illustrated in FIG. 1, the insertion portion 2 includes a distal end portion 6, a bending portion 7, and a flexible tube portion 8. The distal end portion 6 is located at the distal end of the insertion portion 2, the bending portion 7 is provided continuously with the proximal end of the distal end portion 6, and the flexible tube portion 8 has flexibility and is provided continuously with the proximal end of the bending portion 7.

Figure 2:
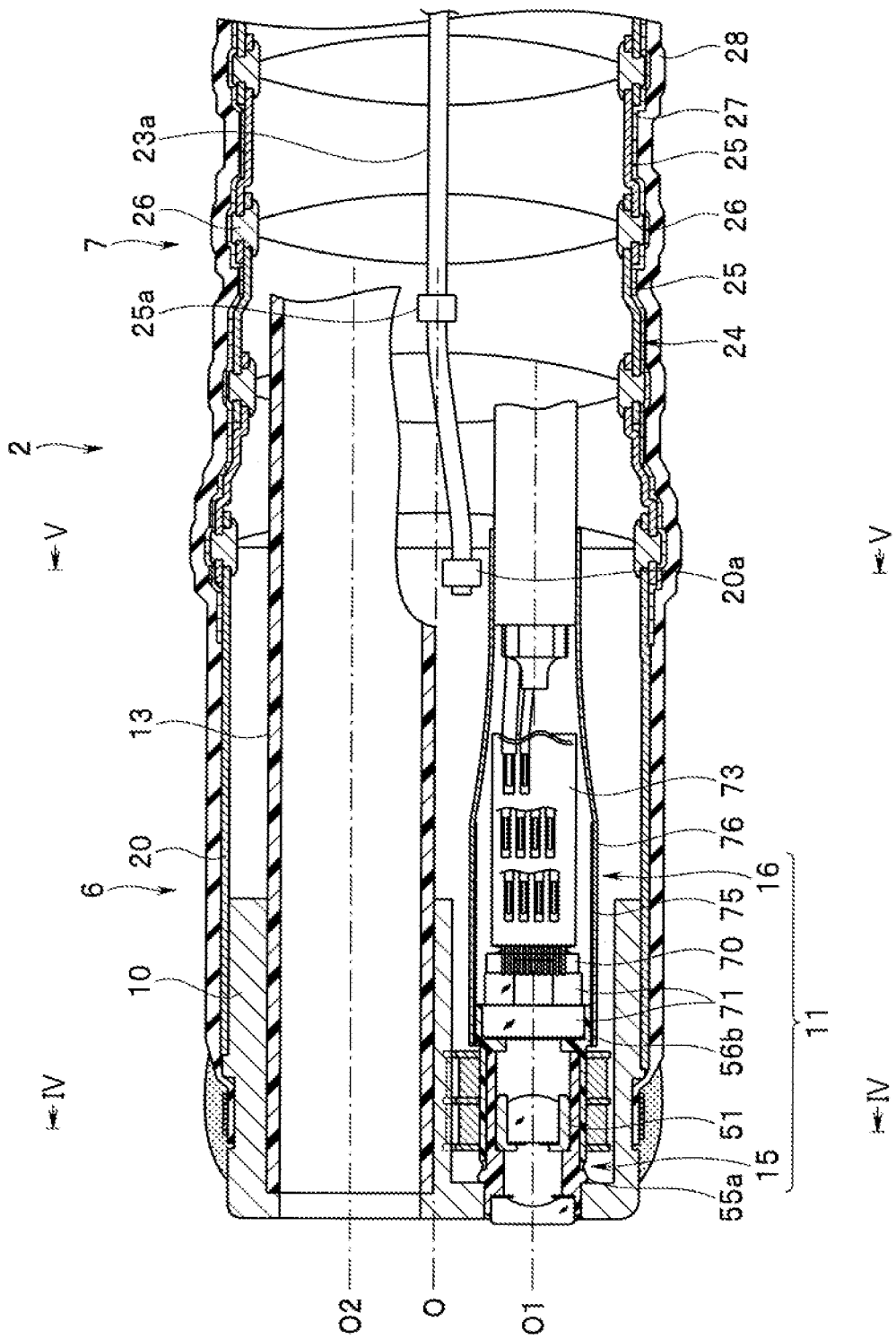
FIG. 2 is a cross-sectional view of essential parts of a distal end portion and a bending portion.

As illustrated in FIG. 2, the distal end portion 6 is provided with a distal end frame 10 made of metal or resin.

Figure 3:
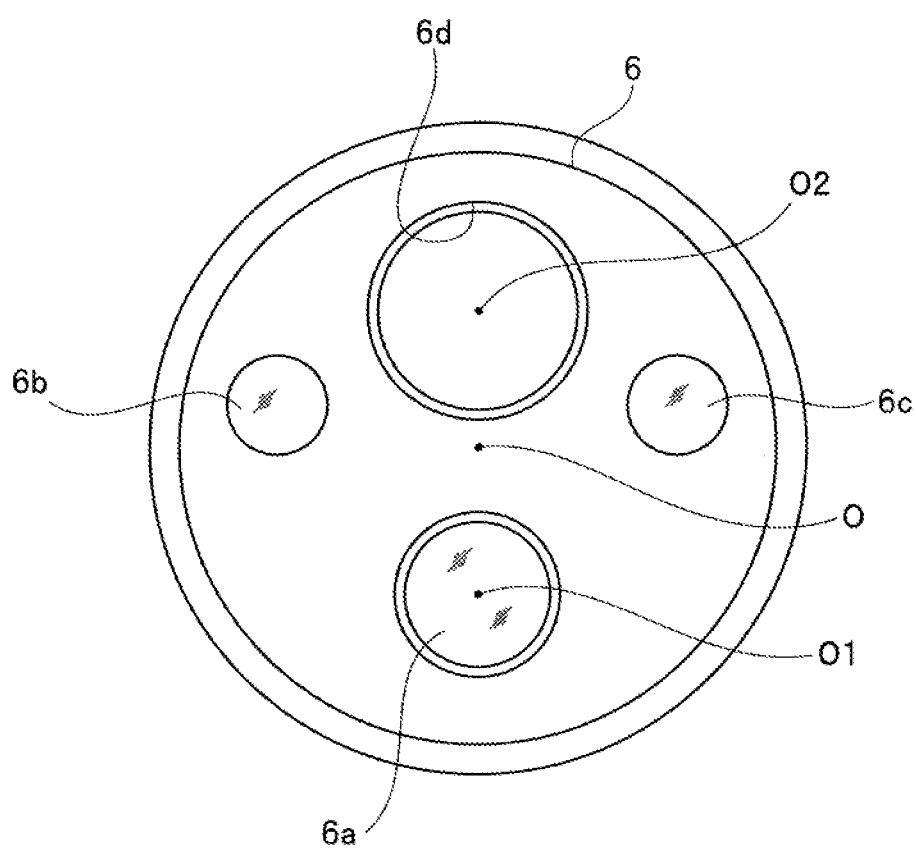
FIG. 3 is an end view of the distal end portion.

As illustrated in FIG. 3, the distal end portion 6 includes, on the distal end surface thereof, an observation window 6a for observing a subject, first and second illumination windows 6b, 6c for applying illumination light to the subject, and a treatment instrument channel port 6d.

Figure 4:
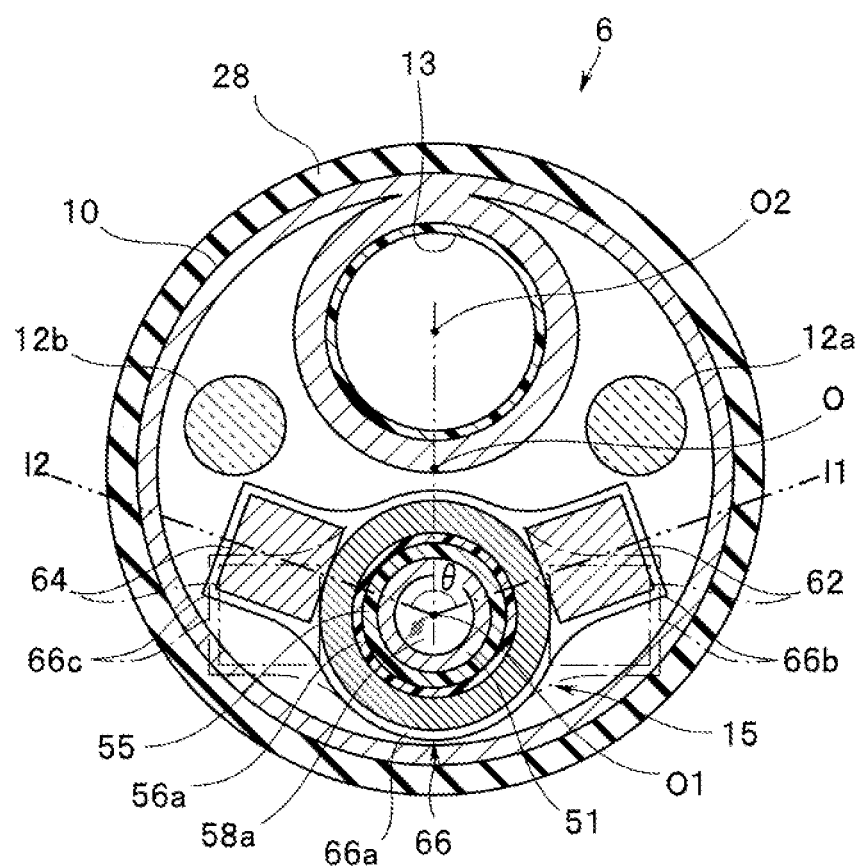
FIG. 4 is a cross-sectional view taken along the line IV-IV in FIG. 2.

In addition, as illustrated in FIG. 4, in the distal end frame 10, an image pickup unit 11, first and second light guides 12a, 12b, and a treatment instrument channel 13 are held. The image pickup unit 11 forms the observation window 6a (as shown in FIG. 3). The first and second light guides 12a, 12b are first and second internal components that supply illumination light to the first and second illumination windows 6b, 6c. The treatment instrument channel 13 is a channel communicating with the treatment instrument channel port 6d.

The image pickup unit includes, for example, an optical unit 15 configured to be capable of switching the focal length between two different focal lengths, and an image pickup device unit 16 configured to pick up an image formed by the optical unit 15.

Note that, in the present embodiment, up, down, left, and right directions are defined for the distal end portion 6 (and insertion portion 2) in correspondence with up, down, left, and right directions of an image picked up by the image pickup unit 11, for example.

The bending portion 7 is configured to actively bend in the up and down directions in accordance with an operation input to the operation portion 3 by an operator.

Specifically, the bending portion 7 according to the present embodiment includes a bending piece group 24 in which a plurality of bending pieces 25 are continuously provided in a line on the proximal end side of a distal-most bending piece 20. In the bending piece group 24, the distal-most bending piece 20 and the respective bending pieces 25 are coupled such that the bending pieces adjacent to each other longitudinally are rotatable with respect to each other with a pair of left and right pivotally supporting portions 26.

In addition, among the plurality of bending pieces 25 that constitute the bending piece group 24, predetermined bending pieces 25 are provided with wire guides 25a. One of a first pulling wire 23a and second pulling wire 23b, each of which is inserted in the insertion portion 2, is inserted through the respective wire guides 25a. The first and second pulling wires 23a, 23b are pulled or relaxed in response to an operation input to the operation portion 3 by the operator, thereby enabling the bending piece group 24 (bending portion 7) to bend in the up and down directions.

In the bending piece group 24 configured as described above, not only the first and second pulling wires 23a, 23b, but also a signal cable 11a extended from the image pickup unit 11, the first and second light guides 12a, 12b, the treatment instrument channel 13, and the like are inserted.

The outer circumference of the bending piece group 24 is covered with a bending rubber 28, with a braid 27 interposed therebetween.

The flexible tube portion 8 includes a spiral tube (not illustrated) having a flexibility and configured to he passively bendable. The distal end side of the spiral tube is coupled to the bending piece 25 located on the proximal-most position in the bending piece group 24. The outer circumference of the spiral tube is covered with an outer cover.

As illustrated in FIG. 1, the operation portion 3 includes a break prevention portion 35, a grasping portion 36, and an operation portion main body 37.

The break prevention portion 35 is connected to the flexible tube portion 8 so as to cover the proximal end of the flexible tube portion 8.

The grasping portion 36 has a shape that can be grasped with a hand of an operator, and provided continuously with the proximal end side of the break prevention portion 35.

The grasping portion 36 includes, on the distal end side thereof, a treatment instrument insertion portion 38. The treatment instrument insertion portion 38 includes a treatment instrument insertion port 38a through which various kinds of treatment instruments (not illustrated) can be inserted. In the grasping portion 36, the proximal end side of the treatment instrument channel 13 is communicated with the treatment instrument insertion port 38a. In addition, a forceps plug (not illustrated) is attachable to and detachable from the treatment instrument insertion portion 38. The forceps plug is a lid member for blocking the treatment instrument insertion port 38a.

The operation portion main body 37 is provided continuously with the proximal end side of the grasping portion 36. The operation portion main body 37 is provided with a bending lever 39. The bending lever 39 causes the bending portion 7 to bend in the up and down directions by pulling or relaxing the first and second pulling wires 23a, 21b.

In addition, the operation portion main body 37 includes a plurality of operation buttons 40 to which various kinds of functions of the endoscope 1 are assigned. In the present embodiment, for example, a function for switching the focal length of the optical unit 15 is assigned to one of the plurality of operation buttons 40.

The universal cable 4 is extended from a side portion of the operation portion main body 37. Various kinds of cables including the signal cable 11a, the light guides 12, and the like are inserted through the universal cable 4.

In addition, the universal cable 4 includes, at the extension end thereof, a connector 5 with which the various kinds of cables and the light guides 12 are connectable respectively to the video processor and the light source apparatus (neither of which is illustrated).

Next, detailed description will be made below on the image pickup unit 11 according to the present embodiment.

For example, as illustrated in FIGS. 3, 4, the optical unit 15 of the image pickup unit 11 and the treatment instrument channel 13 in the present embodiment are held in the distal end portion 6 (that is, the distal end frame 10) such that the optical axis (photographing optical axis) O1 of the optical unit 15, the central axis of the distal end portion 6, and the central axis O2 of the treatment instrument channel 13 are linearly aligned.

In other words, as illustrated in FIG. 2, for example, the optical unit 15 and the treatment instrument channel 13 are arranged such that both the optical axis O1 of the optical unit 15 and the central axis O2 of the treatment instrument channel 13 are located on a cut surface, which includes the central axis O of the distal end portion 6, in the longitudinal direction.

As illustrated in FIGS. 3 and 4, the optical unit 15 is arranged inside the distal end portion 6 such that the photographing optical axis O1 is parallel to the central axis O along the longitudinal direction of the distal end portion 6.

As illustrated in FIGS. 6 to 9, the optical unit 15 includes a fixed frame 50, a movable frame 51, and an actuator 52. The fixed frame 50 is fixed to the inside of the distal end frame 10. The movable frame 51 is configured to be movable forward and backward in the direction of the photographing optical axis O1 in the fixed frame 50. The actuator 52 drives the movable frame 51 from the outside of the fixed frame 50.

The fixed frame 50 includes a first fixed frame 55 formed in a substantially cylindrical shape, and a second fixed frame 56 formed in a substantially cylindrical shape and fitted to the outer circumference of the first fixed frame 55 from the proximal end side.

The first fixed frame 55 is made of a non-magnetic material. An outward flange 55a is provided on the outer circumference of the first fixed frame 55 so as to be located closer to the distal end. A part of the first fixed frame 55, which is on the distal end side with respect to the outward flange 55a, is fixed in a holding hole provided in the distal end frame 10, thereby enabling the first fixed frame 55 to be held in the distal end frame 10.

Figure 8:
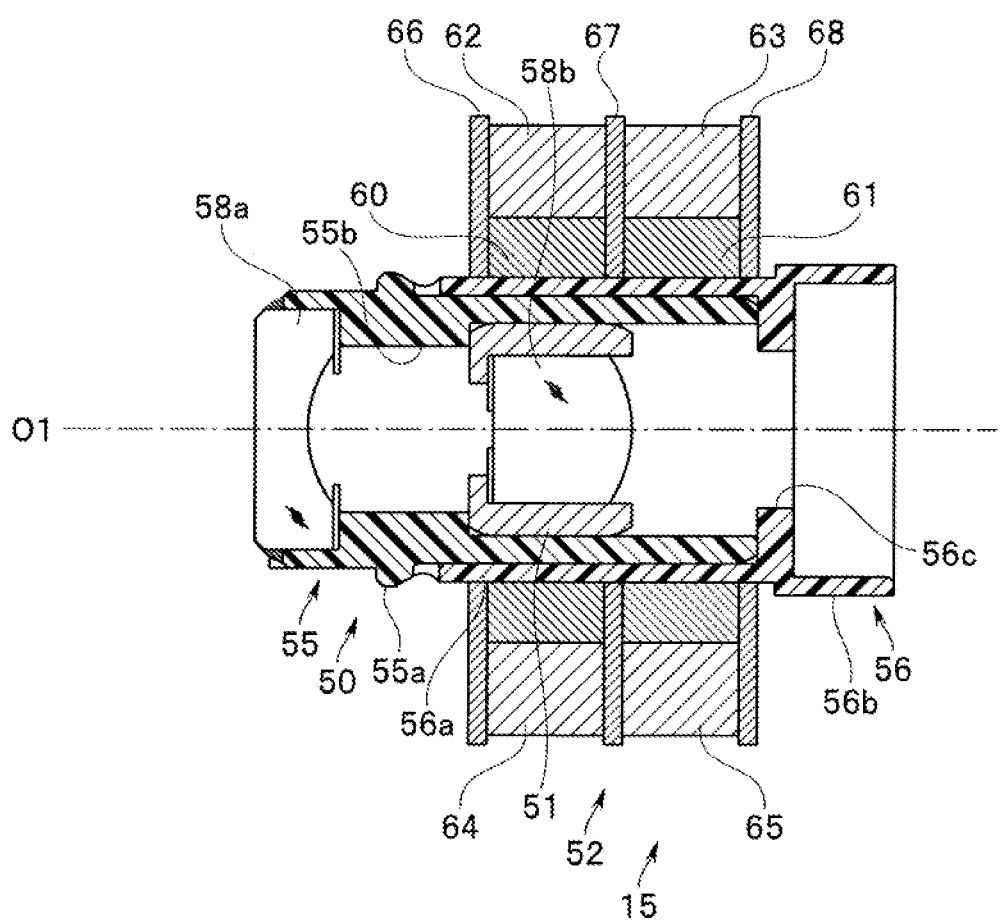
FIG. 8 is a cross-sectional view taken along the line A-A in FIG. 7 when a movable lens frame is on a distal end side.
Figure 9:
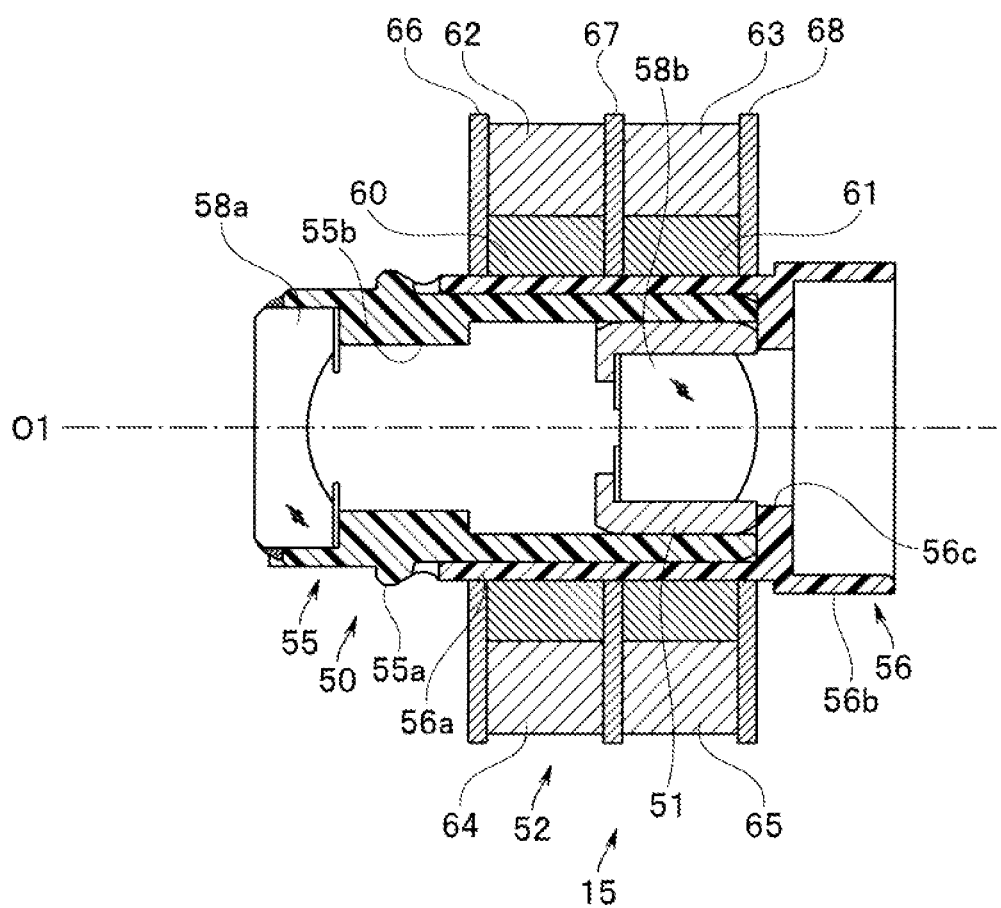
FIG. 9 is a cross-sectional view taken along the line A-A in FIG. 7 when the movable lens frame is on a proximal end side.

In addition, a first stopper 55b is provided on the inner circumference of the first fixed frame 55 so as to be located closer to the distal end. The first stopper 55b is configured to restrict the movement of the movable frame 51 to the distal end side. The first stopper 55b is configured, for example, by an inward flange that protrudes to the inner side of the first fixed frame 55. A fixed lens 58a is held in the first fixed frame 55 at a position on the distal end side with respect to the first stopper 55b. The fixed lens 58a constitutes a photographing lens which is an optical system of the optical unit 15. Although each of the examples illustrated in FIGS. 8 and 9 shows the configuration in which the single fixed lens 58a is held in the first fixed frame 55, it is needless to say that a plurality of fixed lenses may be held in the first fixed frame 55.

The second fixed frame 56 is made of a non-magnetic material. The second fixed frame 56 includes a fitting frame 56a and a coupling frame 56b. The fitting frame 56a has the inner circumferential surface that can be fitted to the outer circumferential surface of the first fixed frame 55. The coupling frame 56b supports the image pickup device unit 16 at the proximal end side of the fitting frame 56a.

A second stopper 56c is provided on the inner circumference of the second fixed frame 56 so as to be located, for example, at a border part between the fitting frame 56a and the coupling frame 56b. The second stopper 56c is configured to restrict the movement of the movable flame 51 to the proximal end side. The second stopper 56c is configured, for example, by an inward flange that protrudes to the inner side of the second fixed frame 56.

The movable frame 51 is made of a magnetic material. The outer circumferential surface of the movable frame 51 is configured to be slidable with respect to the inner circumferential surface of the first fixed frame 55.

In addition, the movable frame 51 holds inside thereof a movable lens 58b that constitutes the photographing lens of the optical unit 15. Although each of the examples illustrated in FIGS. 8 and 9 shows the configuration in which the single movable lens 58b is held in the movable frame 51, it is needless to say that a plurality of movable lenses may be held in the movable frame 51.

The actuator 52 includes a first coil 60 a second coil 61, first magnets 62, 63, second magnets 64, 65, and three yokes 66, 67, 68. The first coil 60 is arranged on the outer circumference of the second fixed frame 56. The second coil 61 is arranged on the outer circumference of the second fixed frame 56 so as to align with the first coil 60 in the direction of the photographing optical axis O1. The first magnets 62, 63, as a first magnetic field generation section, are arranged, in a protruded manner, respectively on the outer circumference of the first coil 60 and on the outer circumference of the second coil 61. The second magnets 64, 65, as a second magnetic field generation section, are arranged, in a protruded manner, respectively on the outer circumference of the first coil 60 and on the outer circumference of the second coil 61. The three yokes 66, 67, 68 are disposed sequentially so as to be located on the front and back of the first coil 60 and the first and second magnets 62, 64, and on the front and back of the second coil 61, and the first and second magnets 63, 65.

Each of the first and second coils 60, 61 is formed by winding a metal wire such as a copper wire on the outer circumference of the fitting frame 56a of the second fixed frame 56.

The first magnets 62, 63 and the second magnets 64, 65 are each a permanent magnet having a rectangular parallelepiped shape. These magnets are arranged on the outer circumference of the first coil 60 and on the outer circumference of the second coil 61 such that the magnetic poles of the magnets are arranged along the photographing optical axis O1.

Specifically, the first magnet 62 provided on the outer circumference of the first coil 60 and the first magnet 63 provided on the outer circumference of the second coil 61 are arranged in a line such that the S-poles and the N-poles are alternately arranged along the photographing optical axis O1. Similarly, the second magnet 64 provided on the outer circumference of the first coil 60 and the second magnet 65 provided on the outer circumference of the second coil 61 are arranged in a line such that the S-poles and the N-poles are alternately arranged along the photographing optical axis O1.

Each of the yokes 66, 67, 68 is configured by a metal plate on which an annular portion, a first protruding portion, and a second protruding portion are integrally farmed. The annular portions 66a, 67a, 68a of the yokes 66, 67, 68 correspond to the first and second coils 60, 61. The first protruding portions 66b, 67b, 68b of the yokes 66, 67, 68 protrude respectively from the annular portions 66a, 67a, 68a in a radially outward direction so as to correspond to the first magnets 62, 63. The second protruding portions 66c, 67c, 68c of the yokes 66, 67, 68 protrude respectively from the annular portions 66a, 67a, 68a, in a radially outward direction so as to correspond to the second magnets 64, 65.

The first and second coils 60, 61 are connected with a power supply line, not illustrated. The conductive direction of the power to be supplied to each of the first and second coils 60, 61 can be switched according to the operation input to the operation button 40, for example. When the direction of the magnetic field generated in each of the first and second coils 60, 61 is switched by the power conduction control, dielectric effect is generated between the magnetic field of the first coil 60 and the magnetic fields of the corresponding first and second magnets 62, 64, and between the magnetic field of the second coil 61 and the magnetic fields of the corresponding first and second magnets 63, 65. With the dielectric effect, the movable frame 51 moves forward and backward between the first stopper 55b on the distal end side and the second stopper 56c on the proximal end side in the direction of the photographing optical axis O1 (see FIGS. 8, 9).

Figure 6:
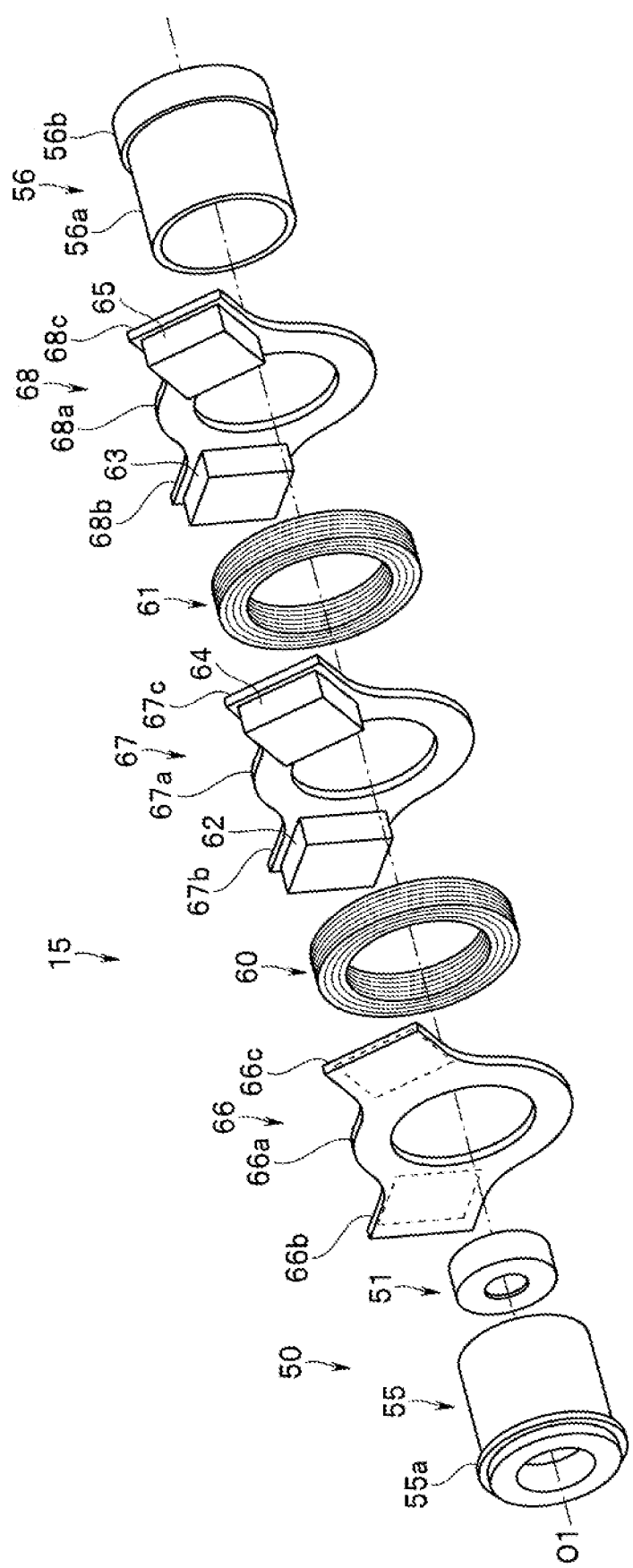
FIG. 6 is an exploded perspective view of an optical unit.
Figure 7:
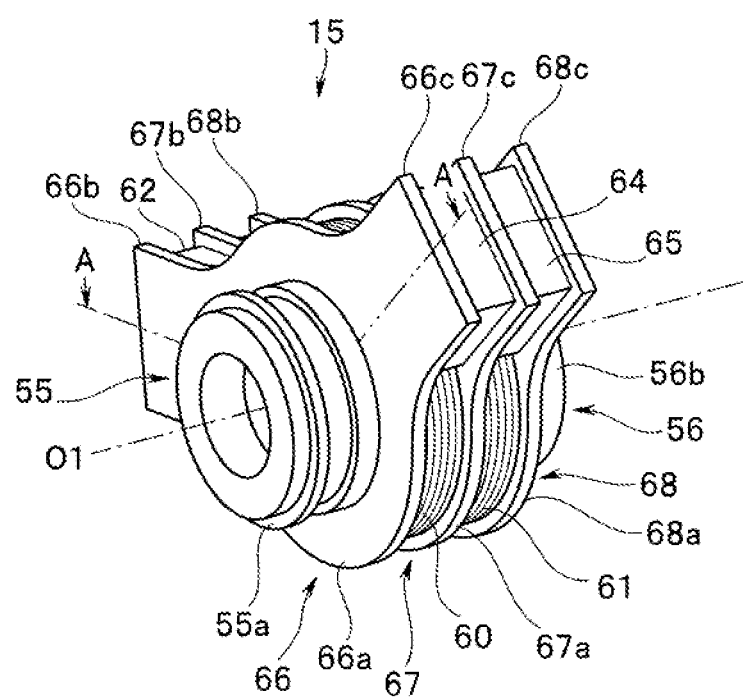
FIG. 7 is a perspective view of the optical unit.

As illustrated in FIGS. 4, 6, and 7, in the optical unit 15 configured as described above, the first magnets 62, 63 and the second magnets 64, 65 are arranged at non-rotationally-symmetric positions with respect to the photographing optical axis O1. In other words, the first magnets 62, 63, the first and second coils 60, 61, and the second magnets 64, 65 are arranged so as to form a gentle "V-shape" when viewed in a plan view.

In the distal end portion 6, the optical unit 15 is arranged such that a region. on a side where the distance between the first magnets 62, 63 and the second magnets 64, 65 on an arc of a circle around the photographing optical axis O1 is short (the region inside the V-shape) faces the treatment instrument channel 13.

In other words, the optical unit 15 is arranged in the distal end portion 6 such that the region of the optical unit 15, which forms an intersection angle θ smaller than 180 degrees enclosed by a first virtual line 11 and a second virtual line 12, faces the treatment instrument channel 13. The first virtual line 11 is extended from the photographing optical axis O1 in the protruding direction of the first magnets 62, 63 and the second virtual line 12 is extended from the photographing optical axis O1 in the protruding direction of the second magnets 64, 65.

With such a configuration, the first magnets 62, 63, the first and second coils 60, 61, and the second magnets 64, 65 are arranged along the inner circumferential arc of the distal end frame 10. The first magnets 62, 63, the first and second coils 60, 61, and the second magnets 64, 65 are thus arranged, to thereby achieve the compact arrangement of the optical unit 15 in the distal end portion 6, compared with the configuration in which the first magnets 62, 63 and the second magnets 64, 65 are linearly arranged at the rotationally symmetric positions with respect to the photographing optical axis O1 (see the one-dot chain lines in FIG. 4).

In the present embodiment, it is preferable that the first magnets 62, 63 and the second magnets 64, 65 are arranged at line-symmetric positions with respect to the linear line connecting the central axis O2 of the treatment instrument channel 13 and the photographing optical axis O1.

In addition, it is preferable that the intersection angle θ is set such that a part of each of the first magnets 62, 63, a part of each of the first and second coils 60, 61, and a part of each of the second magnets 64, 65 are located close to the inner circumferential surface of the distal end frame 10, so as to have substantially the same distance from the inner circumference of the distal end frame 10.

In accordance with such an arrangement of the optical unit 15, the first light guide 12a is arranged inside the distal end frame 10 so as to be located in a region surrounded by the inner circumferential surface of the distal end portion 6 (distal end frame 10), the first magnets 62, 63, and the treatment instrument channel 13. Similarly, the second light guide 12b is arranged inside the distal end frame 10 so as to be located in a region surrounded by the inner circumferential surface of the distal end portion 6 (distal end frame 10), the second magnets 64, 65, and the treatment instrument channel 13.

Figure 5:
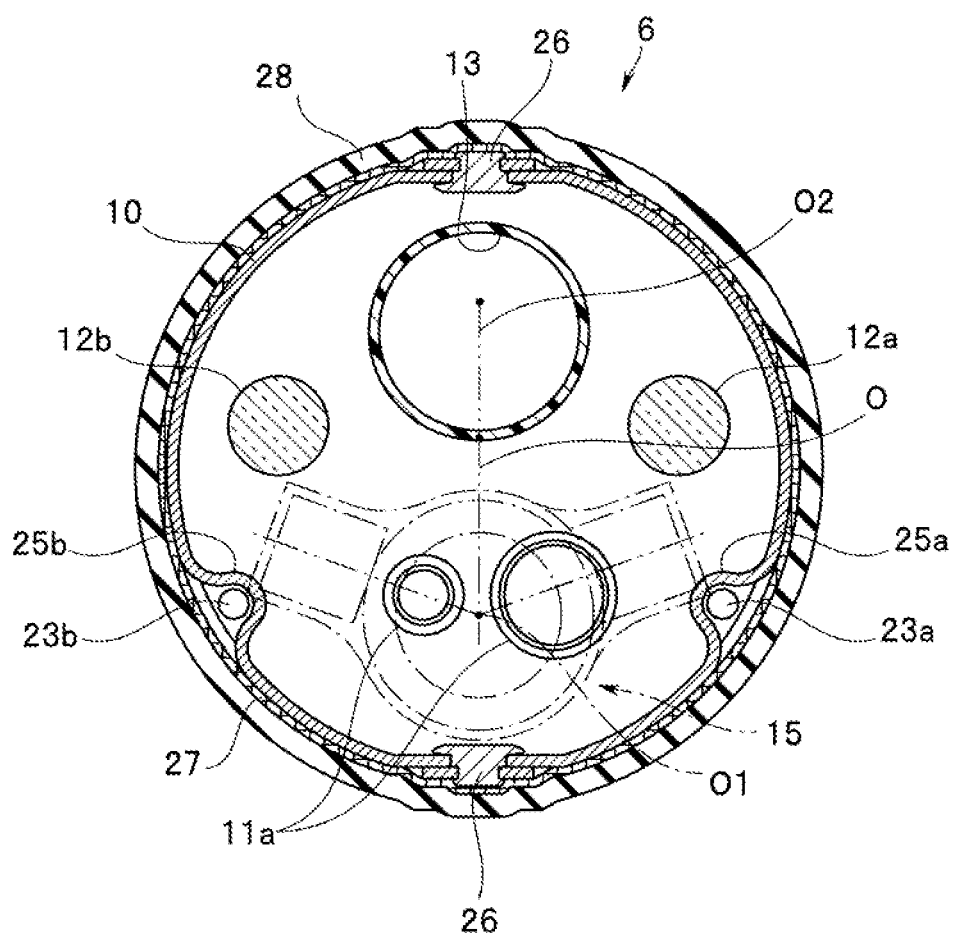
FIG. 5 is a cross-sectional view taken along the line V-V in FIG. 2.

In order to efficiently use the dead space on the proximal end side of the first magnets 62, 63 and the dead space on the proximal end side of the second magnets 64, 65, as illustrated in FIGS. 2 and 5, a first wire fixing portion 20a is arranged in a region including a projection region of the first magnets 62, 63, and a second wire fixing portion 20b is arranged in a region including a projection region of the second magnets 64, 65. Note that, in the present embodiment, the projection region of the first magnets 62, 63 and the projection region of the second magnets 64, 65 refer respectively to the region behind (a virtual region hidden by) the first magnets 62, 63 when viewing the first magnets 62, 63 from the front direction (the distal end direction of the insertion portion 2), and the region behind (a virtual region hidden by) the second magnets 64, 65 when viewing the second magnets 64, 65 from the front direction. The projection regions have cross sections that are the same as the shadows formed on predetermined projection surfaces when applying light to the first magnets 62, 63 and the second magnets 64, 65 from the front.

As illustrated in FIG. 2, the image pickup device unit 16 includes an image pickup device 70 configured by a CCD, a CMOS, or the like.

The image pickup device 70 includes an image pickup surface on which a cover glass 71 is adhered. The cover glass 71 is coupled to the inner circumference of the coupling frame 56b, and thereby the image pickup device 70 is supported by the optical unit 15 and optically coupled with the optical unit 15.

A drive circuit 73 in which various kinds of electronic components are mounted is electrically connected to the proximal end side of the image pickup device 70. The drive circuit 73 is electrically connected with the signal cable 11a.

On the outer circumference of the coupling frame 56b, the distal end side of an exterior frame 75 that covers the outer circumferences of the image pickup device 70 and the drive circuit 73 is coupled. The exterior frame 75 and the outer circumference of the distal end side of the signal cable 11a are covered with a heat shrink tube 76.

According to such an embodiment, the optical unit 15 and the treatment instrument channel 13 are held in the distal end portion 6 such that the photographing optical axis O1, the central axis O of the distal end portion 6, and the central axis O2 of the treatment instrument channel 13 are linearly aligned when viewed from the end face of the distal end portion, the first magnets 62, 63 and the second magnets 64, 65 are arranged at the non-rotationally-symmetric positions with respect to the photographing optical axis O1, and the region of the optical unit 15, which is on the side where the distance between the first magnets 62, 63 and the second magnets 64, 65 on the arc of the circle around the optical axis O1 is short, faces the treatment instrument channel 13. With such a configuration, even in the case where the actuator 52 in which the first magnets 62, 63 and the second magnets 64, 65 each protrude in the radially outward direction of the optical unit 15 is used, the optical unit 15 can be efficiently arranged in the distal end portion 6 without increasing the outer diameter of the distal end portion 6.

In other words, among the internal components arranged in the distal end portion 6, the optical unit 15 and the treatment instrument channel 13, each of which has a large diameter, are arranged such that the photographing optical axis O1, the central axis O of the distal end portion 6, and the central axis O2 of the treatment instrument channel 13 are linearly aligned when viewed from the end face of the distal end portion, to thereby be capable of achieving an efficient arrangement of the internal components in the distal end portion 6.

In such an arrangement, the first magnets 62, 63 and the second magnets 64, 65 are arranged at the non-rotationally-symmetric positions with respect to the photographing optical axis O1, and the region of the optical unit 15, which is on the side where the distance between the first magnets 62, 63 and the second magnets 64, 65 on the arc of the circle around the optical axis O1 is short, faces the treatment instrument channel 13, to thereby prevent the first magnets 62, 63 and the second magnets 64, 65 from interfering with the distal end frame 10, which enables the internal components to be arranged more efficiently in the distal end portion 6.

In addition, the first magnets 62, 63 and the second magnets 64, 65 are arranged at the two locations on the outer circumference of the optical unit 15, to thereby be capable of ensuring a sufficient driving force and a sufficient holding force for the movable frame 51 by the actuator 52. Furthermore, the first magnets 62, 63 and the second magnets 64, 65 are arranged at the non-rotationally-symmetric positions with respect to the photographing optical axis O1, to thereby enable the movable frame 51 to be pressed against one side of the fixed frame 50. Such a configuration prevents a backlash of the movable frame 51, to thereby be capable of achieving stable optical characteristics.

Figure 10:
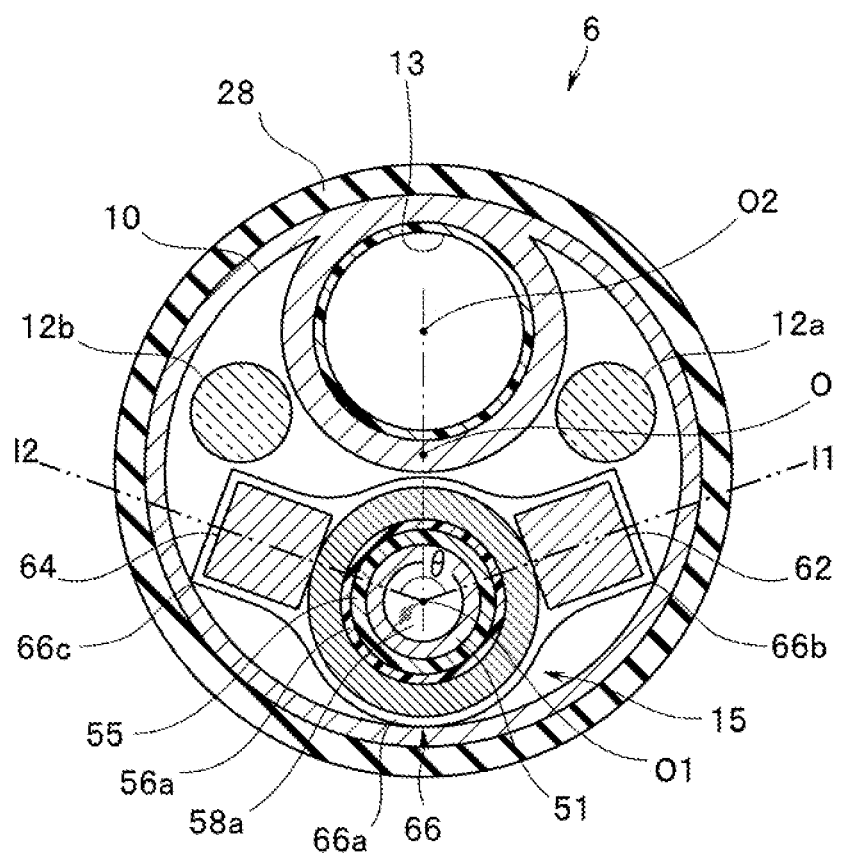
FIG. 10 relates to a second modification and is a cross-sectional view of an essential part of a distal end portion.

In the present embodiment, as illustrated in FIG. 10, for example, the optical unit 15 can also be configured such that a part of each of the first magnets 62, 63, a part of each of the first and second coils 60, 61, and a part of each of the second magnets 64, 65 (actually, a part of each of the first protruding portions 66b, 67b, 68b, a part of each of the annular portions 66a, 67a, 68a, and a part of each of the second protruding portions 66c, 67c, 68c) are all brought into contact with the inner circumferential surface of the distal end frame 10.

With such a configuration, it is possible to more efficiently reduce the diameter of the distal end portion 6.

Figure 11:
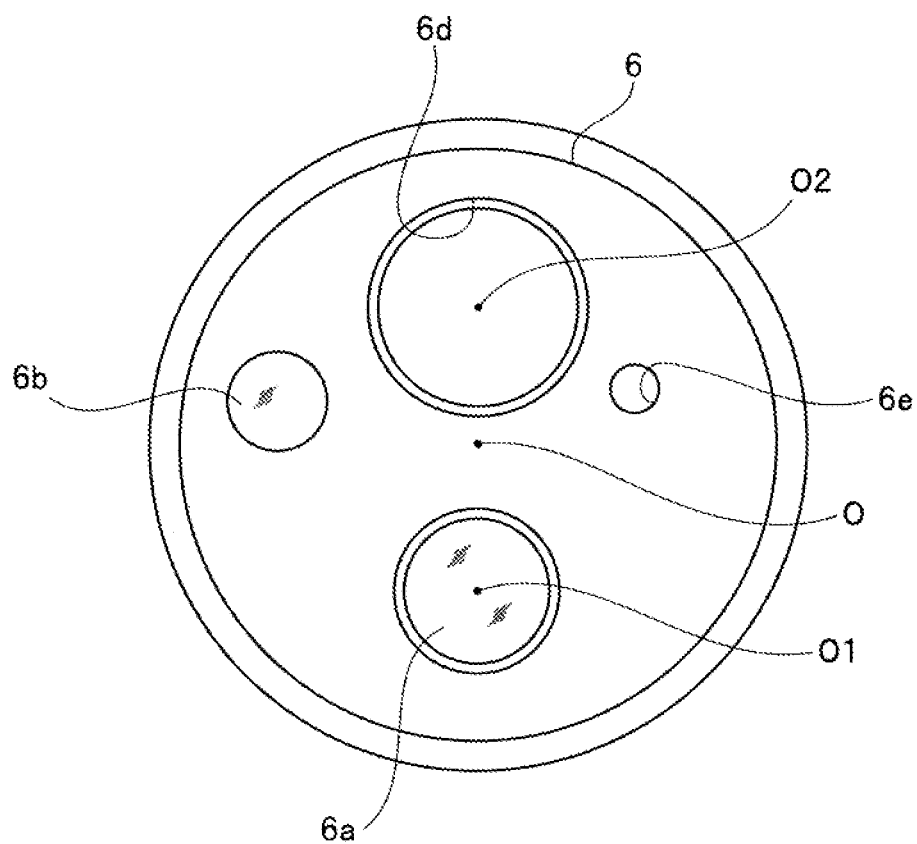
FIG. 11 relates to the second modification and is an end view of the distal end portion.
Figure 12:
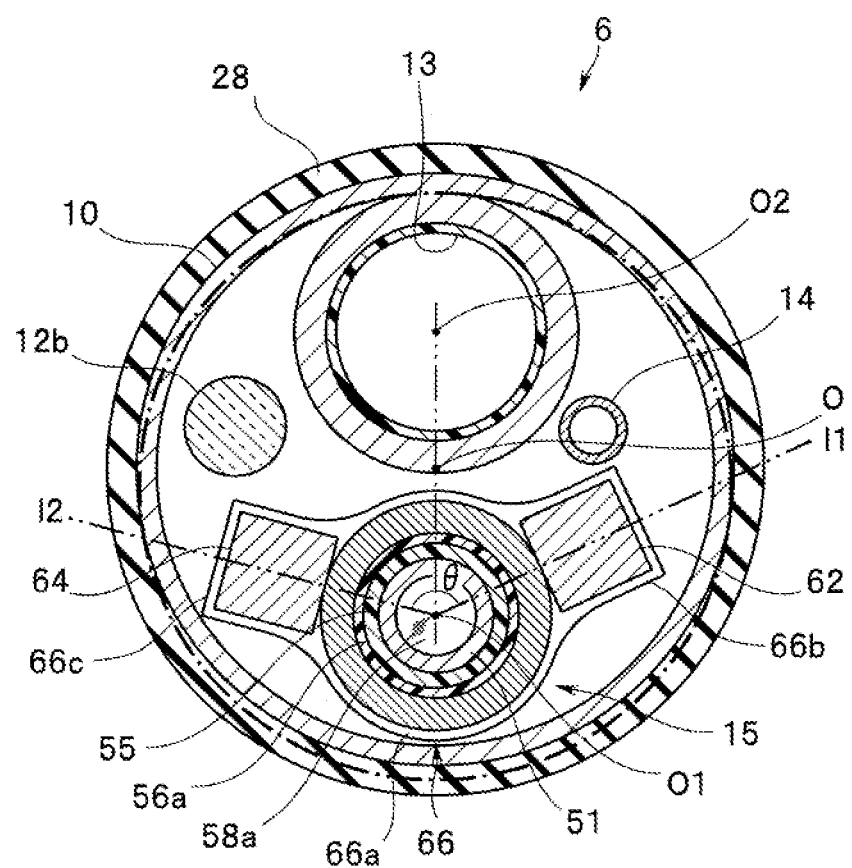
FIG. 12 relates to a third modification and is a cross-sectional view of an essential part of a distal end portion.

Furthermore, as illustrated in FIGS. 11 and 12, for example, instead of the second illumination window 6c, an air/water feeding port 6e can be arranged on the distal end surface of the distal end portion 6, and instead of the second light guide 12b, an air/water feeding tube 14 can be arranged, as the second internal component, in the distal end portion 6.

In this case, in order to efficiently secure necessary spaces in accordance with the difference in the outer diameters of the first light guide 12a and the air/water feeding tube 14, the first magnets 62, 63 and the second magnets 64, 65 can be arranged at non-symmetric positions with respect to a linear line connecting the central axis O2 of the treatment instrument channel 13 and the photographing optical axis O1.

Figure 13:
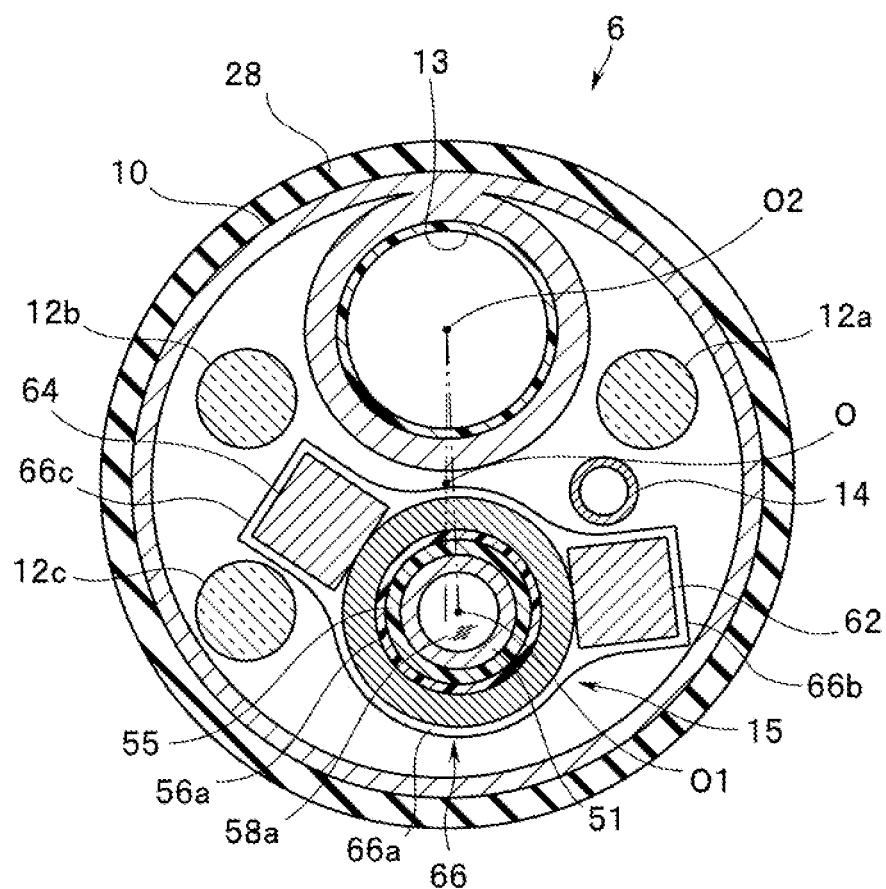
FIG. 13 relates to a fourth modification and is a cross-sectional view of an essential part of a distal end portion.

Furthermore, as illustrated in FIG. 13, for example, in order to efficiently secure spaces for the first light guide 12a, the second light guide 12b, a third light guide 12c, and the air/water feeding tube 14, the first magnets 62, 63 and the second magnets 64, 65 may be arranged at non-symmetric positions with respect to the linear line connecting the photographing optical axis O1 of the optical unit 15 and the central axis O2 of the treatment instrument channel 13, and the optical unit 15 and the treatment instrument channel 13 may be arranged such that the linear line connecting the photographing optical axis O1 of the optical unit 15 and the central axis O2 of the treatment instrument channel 13 is located on a cut surface, which does not include the central axis O of the distal end portion 6, in the longitudinal direction.

Note that the present invention is not limited to the above-described embodiment and each of the modifications, but various modifications and changes are possible, and such modifications and changes are also within the technical range of the present invention.

Although the actuator 52 is configured by the two coils and a pair of magnets in the above-described embodiment, for example, the actuator 52 can be configured by one coil or three or more coils and a pair of magnets.

What is claimed is:

1. An endoscope comprising an insertion portion comprising a distal end portion, the distal end portion comprising an optical unit and a channel inside the distal end portion,
the optical unit comprising:
a fixed frame made of a non-magnetic material;
a movable frame made of a magnetic material and configured to hold one or more lenses that constitute a photographing lens, the movable frame being arranged movably in the fixed frame; and
an actuator configured to drive the movable frame along an optical axis of the photographing lens,
wherein the actuator comprises,
a coil wound around the fixed frame, and
a first magnet and a second magnet that are arranged, in a protruded manner, on an outer circumference of the coil,
the first magnet and the second magnet are arranged in a circumferential direction of the coil at non-rotationally-symmetric positions around the optical axis, and a region in the circumferential direction of the coil faces an outer circumference of the channel, the region being on a side where a distance between the first magnet and the second magnet in the circumferential direction of the coil is short by non-rotationally-symmetric arrangement of the first magnet and the second magnet.

2. The endoscope according to claim 1, wherein
the optical unit and the channel are held in the distal end portion such that an optical axis of the optical unit, a central axis of the distal end portion, and a central axis of the channel are linearly aligned when viewed from an end face of the distal end portion.

3. The endoscope according to claim 1, further comprising:
a first internal component arranged in a region surrounded by an inner circumferential surface of the distal end portion, the first magnet, and the channel;
a second internal component arranged in a region surrounded by the inner circumferential surface of the distal end portion, the second magnet, and the channel,
wherein the first internal component and the second internal component are light guides.

4. The endoscope according to claim 1, further comprising:
a first internal component arranged in a region surrounded by an inner circumferential surface of the distal end portion, the first magnet, and the channel;
a second internal component arranged in a region surrounded by the inner circumferential surface of the distal end portion, the second magnet, and the channel,
wherein one of the first internal component and the second internal component is a light guide, and
another one of the first internal component and the second internal component is an air/water feeding channel.

5. The endoscope according to claim 1, wherein
an intersection angle formed by a first virtual line extended from the optical axis to a protruding direction of the first magnet and a second virtual line extended from the optical axis to a protruding direction of the second magnet is an angle at which a part of the first magnet, a part of the second magnet, and a part of the coil are constrained with or contact with the inner circumferential surface of the distal end portion.

6. The endoscope according to claim 1, wherein
the first magnet and the second magnet are arranged at line-symmetric positions with respect to a linear line connecting a central axis of the channel and the optical axis.

7. The endoscope according to claim 1, further comprising:
a first pulling wire for causing a bending portion to bend in a first direction, the bending portion being provided continuously with the distal end portion;
a second pulling wire for causing the bending portion to bend in a second direction which is opposite to the first direction;
a first fixing portion configured to fix the first pulling wire to an inside of the distal end portion; and
a second fixing portion configured to fix the second pulling wire to the inside of the distal end portion,
wherein the first fixing portion is arranged in a region including a projection region of the first magnet, on a proximal end side of the first magnet, and the second fixing portion is arranged in a region including a projection region of the second magnet, on a proximal end side of the second magnet.

8. The endoscope according to claim 1, wherein
no magnets other than the first magnet and the second magnet are provided in the circumferential direction of the coil.

* * * * *